US00PP09954P

United States Patent [19]

Mak

[11] Patent Number: Plant 9,954

[45] Date of Patent: Jul. 8, 1997

[54] LILY PLANT 'VILLANOVA'

[76] Inventor: Johan A. Mak, 5595 Halls Ferry Rd., Independence, Oreg. 97351

[21] Appl. No.: 638,465

[22] Filed: Apr. 24, 1996

[51] Int. Cl.[6] ..... A01H 5/00

[52] U.S. Cl. ..... Plt./87.4

[58] Field of Search ..... Plt./87.4

*Primary Examiner*—James R. Feyrer

[57] ABSTRACT

A new variety of hybrid lily plant bearing large upright-facing flowers of excellent form and long persistence, both on the plant and as cut flowers. The flowers of the new plant are particularly characterized by their pink coloration shading into a wide solid red band at the midrib, their large size and heavy substance, their "flat-faced" form, created by broad tepals which recurve only at the tips, their upright to semi-upright orientation, the sharply ascending pedicels of the upper flowers, and the long buds. This combination is completely new in the Oriental Hybrid divisions of the lilies suited to forcing and to mass commercial cultivation. The variety is highly resisant to fusarium disease as well as botrytis. The bulbs may be precooled and forced for cut-flower production. In comparison to the most of other Oriental varieties, the bulbs of this new hybrid lily can be stored in a cooler for a longer time and still produce excellent cut-flower stems when forced into flower out of season. The clone is vigorous and is a good grower and propagator.

1 Drawing Sheet

BACKGROUND OF THE INVENTION

My new variety of lily plant originated as a seedling which first flowered in 't Zand, Netherlands, in 1987. The breeding efforts had as their objective the production of large-flowered upright and semi-upright Oriental hybrids in bicolor combinations of pink, white, and yellow, with pigmented papillae, suited to forcing into flower out of season, heretofore unknown in the lily breeding art. I achieved the desired objective by intercrossing selected upright and semi-upright pink Oriental seedlings suited to forcing for year-round use as cut-flowers and carrying the recessive gene for a small yellow band. The flowers of my new lily are characterized by an upright orientation, large size and broad-tepalled "flat-faced" form with only the tips of the tepals recurving, an unusually thick substance, ruffled tepal margins, and a distinctive soft pink coloration shading into a small yellow banded midrib, with deeper magenta-rose papillae, unique among Oriental hybrid lilies. The pedicels of the upper flowers are sharply ascending. It possesses unusually strong, stout stems. In addition, the clone possesses to a high degree desirable characteristics of hybrid vigor. The clone is a good grower and propagator, as observed at 't Zand, Netherlands, and at Salem, Oreg. My new variety of lily plant has been asexually reproduced by me and under my direction at 't Zand, Netherlands, and at Independence, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrated the flower form, the tepal arrangement, the ascending pedicels connecting the flower to the stem, the long buds, and in particular the novel and distinctive "flat-faced" flower form with lightly ruffled tepal margins, the upright and semi-upright orientation of the flowers, and their soft soft pink coloration shading into a wide solid red banded midrib, accented by deeper magenta rose papillae on the basal half of each tepal.

DESCRIPTION OF THE VARIETY

The following is a detailed description of my new variety of Oriental hybrid lily, with nomenclature according to the International lily register (Royal Horticultural Society of London, Second Edition, 1969, and with color designations according to the Colour Chart of The Royal Horticultural Society, published by the Society in 1969).

THE PLANT

Origin: Seedling

Seed parent: Selected unnamed Oriental hybrid seedling.

Pollen parent: Selected unnamed Oriental hybrid seedling.

Commercial classification: Hybrid Lilium clone.

Horticultural classification: Division VII-B to VII-d, flat-shaped Oriental hybrid lily, but also recurved flower according to the Horticultural Classification of Lilies, Royal Horticultural Society of London.

Form: Single stem, erect and stately.

Height: 80 to 135 cm. from bulbs 14 to 18 cm. in circumference, provided their light levels are adequate; low light levels may cause "stretching"

Growth: Vigorous and upright.

Foliage quantity: Abundant.

Size of leaf: Unusually broad, 4 to 7 cm. wide×10 to 14 cm. long.

Shape of leaf: Lanceolate (pointed).

Texture: Leathery and glossy.

Color: Dark green, lighter on lower side.

Bulb size: Any size, ranging to 25 1 cm. circumference commercially.

Bulb color: White, with flushes of pink or yellow after exposure to light.

THE BUD

Form: Slender, elongate, and pointed at the tip.

Size: 9 to 13 cm. long and 9 to 12 cm. in circumference just prior to opening

Opening: Bud opens slowly, in response to morning light; this takes about one hour.

Color: Ivory white to pink (R.H.S. CC red 66 C).

Pednucle: Averages 12 to 15 cm. but it may elongate if light levels are too low or it bulbs have been improperly stored prior to forcing. Color is medium green with very light plum overlay.

THE FLOWER

Blooming habit: Annually in mid season; flowers once and profusely.

Size: Flowers are large-sized, averaging 16 to 21 cm. in diameter, after recurving at the tips on the second day to 14 to 18 cm. in diameter. The tepals are broad; outer tepals are 2.5 to 3.50 cm. wide, and the inner tepals are 5 to 7 cm. wide.

Borne: In a single raceme inflorescence producing 4 to 6 flowers from a bulb 14 to 16 cm. in circumference.

Shape: Form is flat-faced the first day. The second day after opening, the flower will be flat-faced and recurved at the tip of all the pedals.

Tepalage: Typical of genus Lilium, with 6 imbricated tepals.

Tepal color: Small white edge shading into R.H.S. CC red purple 73 C, depending upon growing, temperatures and light levels, shading into a solid red band of R.H.S. CC red 45 B. The pink color is slightly affected by temperature and light levels; it decreases with high temperatures and low light levels.

Tepal spotting: The basal half of each tepal is spotted with magenta rose papillae of moderate size.

Tepal longevity: Tepals stay on stems about three weeks.

Pedicel length: Average 8 to 12 cm. long.

Pedicel color: Medium green with very light plum overlay.

Pedicel form: Sturdy and ascending, up to 60 degrees from the horizontal in the upper flowers.

Color changes: Red band becomes slightly darker and the edge slightly softer pink as the flowers age. Low light levels and extreme heat may cause the pink pigmentation to decrease.

Appearance: Flower is shiny.

Disease resistance: The flower and plant are resistant to disease; in particular, they are resistant to Fusarium bulb rot and Botrytis blight.

Fragrance: Light sweet fragrance.

Lasting quality: The flower is long lasting, both on the plant and as a cut-flower.

THE REPRODUCTIVE ORGANS

Stamens: Arrangement typical of genus Lilium. Six stamens with soft green to palest pink filaments 8 to 10 cm. long.

Pollen and anthers (dehisced): R.H.S. CC greyed orange 175 A.

Pistil: One in number, 8 to 12 cm. long.

Stigma: R.H.S. CC Black 202D, large in size.

Characteristics of ovary: Characteristics of genus Lilium.

THE FRUIT

Fertility: The fruit bears fertile seed.

Shape: Ovoid.

Color at maturity: Soft brown, sometimes overlaid with soft plum.

My new variety of Oriental hybrid lily most nearly resembles "Stargazer", but it has much larger and thicker, more flat-faced flowers. Its flowers are larger in size as well as a more conspicuous red midrib. Its pedicels are more sharply ascending, its inflorescence is longer, and its stem is taller.

I claim:

1. A new and distinctive variety of Oriental hybrid lily plant substantially as herein shown and described, characterized by its resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in prticular by its unique upright to semi-upright flowers with sharply ascending pedicels, its long and pointed buds, the large flat-faced form of its flowers, which recurve only at the tips, its soft pink coloration shading into a wide solid red band at the midrib, accented with noticeable magenta rose papillae on the basal half of each tepal, a combination unique among Oriental hybrid lilies suited to forcing and to mass commercial cultivation.

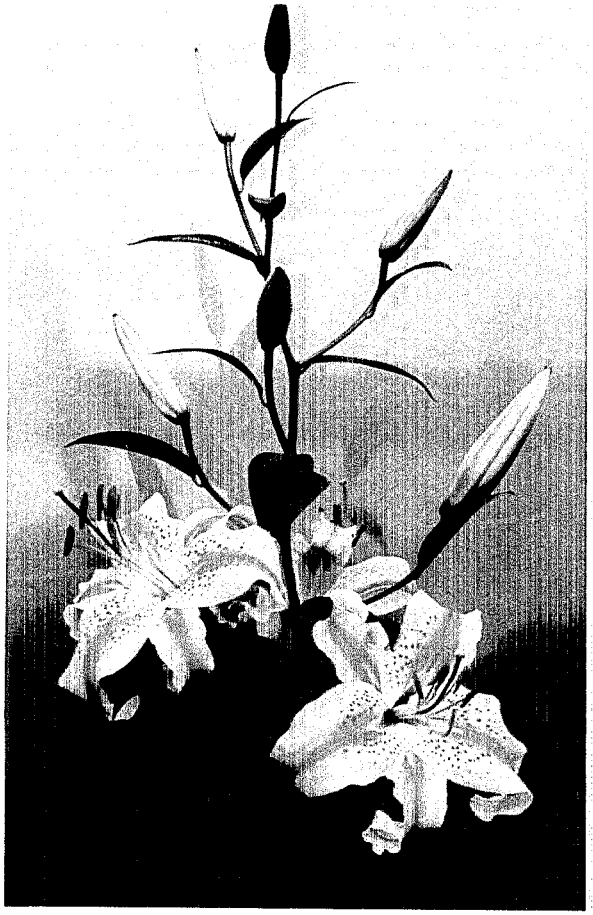

* * * * *